United States Patent
Krumme et al.

(10) Patent No.: US 6,913,766 B1
(45) Date of Patent: Jul. 5, 2005

(54) PREPARATION CONSISTING OF A FILM, SHEET OR WAFER-SHAPED FORM OF ADMINISTRATION WITH A TWO-LAYERED STRUCTURE AND AN INTEGRATED IDENTIFICATION MARKING

(75) Inventors: Markus Krumme, Neuwied (DE); Karin Ludwig, Datzeroth (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 207 days.

(21) Appl. No.: 10/129,833
(22) PCT Filed: Nov. 3, 2000
(86) PCT No.: PCT/EP00/10862

§ 371 (c)(1),
(2), (4) Date: Jul. 10, 2002

(87) PCT Pub. No.: WO01/35931

PCT Pub. Date: May 25, 2001

(30) Foreign Application Priority Data

Nov. 12, 1999 (DE) .......................... 199 54 420

(51) Int. Cl.⁷ .......................... A61F 13/00; A61N 25/34
(52) U.S. Cl. .......................... 424/449; 424/402; 424/443
(58) Field of Search .......................... 424/443, 449, 424/402

(56) References Cited

U.S. PATENT DOCUMENTS

| 5,516,530 A | 5/1996 | Lo et al. |
| 6,106,930 A | * 8/2000 | Ludwig ................. 428/156 |
| 6,165,499 A | * 12/2000 | Kleinsorgen et al. ....... 424/449 |

FOREIGN PATENT DOCUMENTS

| DE | 196 46 836 A1 | 5/1998 |
| EP | 0 398 229 A | 11/1990 |
| WO | 95 09608 A | 4/1995 |
| WO | WO 95/09608 | 4/1995 |
| WO | 98 20859 A | 5/1998 |

* cited by examiner

Primary Examiner—Thurman K. Page
Assistant Examiner—Isis Ghali
(74) Attorney, Agent, or Firm—Birch, Stewart, Kolasch & Birch, LLP

(57) ABSTRACT

A sheet-like, film-like or wafer-like preparation for administering substances affecting flavor or odor and/or substances for care and/or curative substances, comprising a coding of these substances in the form of characters and/or graphic symbols or patterns, with the coding being formed by surface areas of differing thickness, is characterized in that the preparation comprises two differently colored, adjacent layers which have surface areas of differing thickness which are complementary to each other.

16 Claims, 1 Drawing Sheet

PREPARATION CONSISTING OF A FILM, SHEET OR WAFER-SHAPED FORM OF ADMINISTRATION WITH A TWO-LAYERED STRUCTURE AND AN INTEGRATED IDENTIFICATION MARKING

BACKGROUND OF THE INVENTION

1. Field of the Invention

The invention relates to a flat-shaped preparation, consisting of a sheet-like, film-like or wafer-like administration form whose structure comprises two layers, which layers are provided with a coding in the form of characters, graphic symbols or patterns for identifying the substances which can be released therefrom during use. This preparation is especially suited for administering substances affecting flavour or odour and/or care or curative substances. The invention also indicates processes by means of which the above-mentioned administration forms can be provided with codings.

2. Description of the Related Art

Manufacturers of pharmaceutical products are increasingly obliged to identify not only the primary packaging, but also the product itself. This especially applies to medicaments in an administration form aimed at controlling the release of active substance.

According to the prior art, in the case of medicaments in the form of coated tablets, capsules or sheet-like or film-like products such identification or coding is usually accomplished in an additional operation following the actual manufacture, namely by printing or punching of special identification marks or patterns.

In addition to the outlay necessitated by this, with correspondingly increased production costs, the originality and proofness against forgery are not particularly good, especially in the case of printing, as it is relatively easy to apply, or remove, such markings afterwards. Printing has the additional disadvantage of serving exclusively for identification while having no further function, for example in terms of the modification of release or of an increase in the possible loading, and it is therefore relatively expensive.

For tablets, methods of identification are known where during the manufacture relief-like signs or patterns are produced. According to the processes described in U.S. Pat. No. 5,516,530, respectively WO 95/09608, the tablet material is cast as a dispersion into a mould wherein the signs or patterns have been pre-formed. After solidification of the mass under action of pressure, freezing or freeze-drying, a tablet is obtained which has the pre-determined relief-like embossing. It will be readily appreciated that this method is unsuited for providing identification marks on sheet-like, film-like or wafer-like administration forms.

DE-OS 196 46 836 A1 describes a single-layered administration form of the type last-named which is provided with an identification marking or coding. This is provided in the form of thickness gradients, i.e. depressions and elevations, in the flat preparations. In this way a visual effect is produced which is comparable to watermarks. To achieve these patterns, the preparation mass is coated onto an appropriately structured support, or the patterns are applied afterwards, under action of pressure. The described type of identification does, however, have the disadvantage of not being particularly clearly visible. The main reason for this is that it is only monochromatic and can be recognized only because of small light/dark contrasts at its contours. An additional factor is that the thickness gradients making these watermark-like patterns visible are only within the $\mu$m range. In the case of the thin administration forms mentioned, it is not possible to further increase the thickness gradients in order to improve perceptibility.

A further disadvantage, not to be underestimated, of the administration form disclosed in DE-OS 196 46 836 A1 is that by applying the patterns in the form of depressions, the average layer thickness—and thus also the maximum possible loading with active substances—is overall reduced. For administration forms which anyway cannot be highly loaded owing to their dimensions, e.g. film-like administration forms, this disadvantage is particularly significant.

SUMMARY OF THE INVENTION

It was therefore the object of the present invention to provide a preparation having an administration form which is in the form of a sheet, a film or a wafer, and which contains at least one substance from the group consisting of flavors, odorants, therapeutic substances and curative substances, which preparation is provided with an identification or coding in the form of characters, signs/symbols or patterns, but which does not have the disadvantages of the administration forms known from the prior art. It was furthermore an object of the invention to indicate processes which enable a simple and economical manufacture of the administration forms according to the present invention.

Surprisingly, this object is achieved in that flat-shaped, in particular sheet-like, film-like or wafer-like preparations, possess a two- or multi-layered structure, where two adjacent layers are of different colour and/or have surface areas of differing thickness which are complementary (or reciprocal) to each other.

DETAILED DESCRIPTION

Figure 1:
FIG. 1 shows a cross section of a bilayer medicinal administration form provided with coding.

The term "of differing thickness" refers to differences in thickness within a respective layer of the two layers. Thus, the double-layered preparations according to the invention can also possess surface areas where the two layers are of the same or almost the same thickness.

By means of the patterned thickness differences in the layers of the sheet-like, film-like or wafer-like administration forms, an identification marking is accomplished in the surface of the preparation which is visible to the eye and is similar in its effect to a watermark in a paper-like dispersion.

Because of the special arrangement of two layers which are of complementary shape and of different colour the visual perceptibility of the symbols or patterns, which are produced by the thickness gradients, is considerably improved. A further advantage results from the manifold combinations of colours, it being possible to further increase the perceptibility by appropriate selection of colours (e.g. complementary colours). To produce an optimal visual effect it may be of advantage for the layers to be essentially opaque. In particular cases it may also be advantageous to use transparent layers. The identification markings may be letters, numbers, symbols, logos, pictographs or figurative representations.

The difference in colour of the two layers may be accomplished by differences in terms of colour tone, colour saturation or colour brightness, or by combinations of these parameters. The colours black, white, as well as grey colour tones are also understood as being colours in the sense of the invention. Furthermore, embodiments are also encompassed where one of the two layers is made to be clear-transparent. Since the visual effect is brought about mainly by refraction of light at the phase boundaries of the two layers, minor differences in the colour tone, in the colour saturation or the brightness may cause that the contours of the symbols or patterns, which serve as a coding, are clearly perceptible. In addition, the surface areas of the identification markings, symbols or patterns located inside or, respectively, outside the contours also contrast with each other, on account of the differences in colour tone or colour saturation or colour brightness. Moreover, due to two surface areas of differing thickness and different colour overlying each other, each time two new colours or shades are produced which result from either the one or the other layer being thinner or thicker in the region of overlap. In this way, the perceptibility of the marks or patterns, which are formed as thickness gradients in the two layers, is further enhanced.

In comparison to the conventional, watermark-like identification markings, whose perceptibility is due merely to minimal light/dark contrasts, the present invention makes use of the advantageous properties of colour contrasts. In addition, light-dark contrasts occur here which contribute to the perceptibility of the identification markings. Since the identification according to the present invention—as with conventional watermark-like markings or embossings—also constitutes a coding which is an integral and inseparable part of the pharmaceutical preparation itself, it also offers the advantages resulting therefrom (e.g. proofness against forgery) which are not present in other coding methods, especially in printing.

Especially for medicine forms consisting of thin layers (e.g. film-like or wafer-like administration forms) the type of marking or coding according to the present invention is an advantageous alternative compared to the known methods. Producing identifying patterns or symbols by interaction of two complementary, differently coloured layers not only improves recognizability, but also opens up numerous new possibilities of variation in representation.

Since the layer thickness is substantially constant over the entire surface, it is possible to accomplish optimal loading with active substance. The double-layered structure furthermore enables loading with different active substances or other, different substances of the kind mentioned in the introductory portion of claim 1. Further possibilities result from the fact that the two layers can in different ways be provided with additives which have an effect on the release behaviour.

For certain application purposes it may be useful, or necessary, to equip the double-layered administration form of the present invention with further layers. In order not to interfere with the perceptibility of the coding, layers are preferred here that are essentially transparent.

In one embodiment of the invention the surface areas of differing thickness, especially in the layer that is produced first, are formed under the production conditions while avoiding differences in density or compression. This is preferably achieved by forming the surface areas of differing thickness of the first layer without the action of pressure. Thereafter, the second layer is applied to the first layer in such a manner that it completes the relief-like thickness differences pre-formed in the first layer in a complementary manner.

According to another embodiment of the invention the portions of differing thickness, especially those of the layer which is produced first, are of differing density or compression due to the process of manufacture. This can be accomplished by applying the symbols or patterns of the coding in the already pre-fabricated first layer under action of pressure.

The method according to the invention for producing the preparation involves the symbols or patterns serving as the coding being introduced into the first layer by irreversible deformation in the plastically deformable state.

To produce the areas of differing thickness without action of pressure, the mass used for making the layer is coated onto a support, which has a sequence of depressions and elevations corresponding to the coding (identifying marking or pattern). Such depressions or elevations can be arranged, for example, on a support similar to a pressure or printing plate by grinding or etching.

To accomplish the areas of differing thickness in the first layer without the action of pressure, it is possible to use, for example, appropriately structured embossing rollers or stamps.

When the first layer, with relief-like areas of differing thickness, has been produced, whether with or without action of pressure, the second layer is applied by coating from the solution or melt, namely on that side of the first layer which has the relief-like depressions and elevations. The coating mass used to make the second layer must be selected such that on the one hand it enables good anchorage of the second layer onto the first, structured layer, but on the other hand does not dissolve or melt the first layer.

The term "coating" is understood to refer to any manner of applying a hardenable liquid mass on a carrier by means of knife application, roller application, extrusion or spraying processes.

A further method according to the invention for providing the first layer with pattern-like thickness gradients consists in subjecting the preparation to local temperature differences during drying. This can be accomplished by selectively delivering heated air, with the layer to be dried being located on a support which has a lattice-like pattern or consists of materials with different heat conduction which are so arranged that they can form patterns or identifying markings. By exposure to local temperature differences, thickness differences are produced in the layer in such a way that the material in the warmer zones is thicker and the material in the colder zones is thinner. The temperature differences that may occur locally between the warmer and the colder zones are within a range of 10–100° C., preferably between 30–80° C.

The methods according to the invention may be adapted so as to be continuous or discontinuous. Discontinuous manufacture may, for example, be accomplished by conveying the plastically deformable mass on an adhesively treated conveyor belt and in the process providing it with a marking or pattern for coding by means of a structured embossing roller or by exposure to local temperature differences. Subsequently, the second layer is applied by way of a likewise continuous application process (doctor knife, rollers).

In the case of a discontinuous or intermittent method of manufacture, the coating mass of the first layer may be applied on a correspondingly structured support having a pre-determined area. Alternatively, the markings, patterns or symbols serving as a coding may also be introduced in the plastically deformable first layer by means of a stamp. After hardening thereof, the mass for the second layer is applied to that side of the first layer which is provided with relief-like elevations and depressions, using one of the coating methods mentioned.

In the following, the production of coded, flat-shaped administration forms, i.e. flat-shaped administration forms provided with thickness differences in the form of identifying marks, patterns or symbols, will be explained in more detail by way of examples of embodiments. Here, I, II and III designate three different production methods. These methods involve a sequence of work steps A–E as follows:

A. Production of the Coating Mass

Combining individual components by mixing, dissolving, dispersing, suspending or emulsifying. The solvent, dispersing or suspension agent used is preferably an ethanol-water mixture, but other solvents or solvent mixtures which are readily withdrawable can also be used. An illustrative formulation of a coating mass, which is especially suitable for forming surface areas of differing thickness under action of pressure ("embossing method"), is:

32.8%-wt. of polyvinylpyrrolidone
11.5%-wt. of hydroxypropyl cellulose
6.6%-wt. of titanium dioxide
32.8%-wt. of silicon dioxide
16.4%-wt. of polyethylene glycol 400
and ethanol as solvent An illustrative formulation of a layer mass, which is particularly suited for forming surface areas of differing thickness without action of pressure ("thermal method"), is:

28.6%-wt. of polyvinyl alcohol
7.9%-wt. of titanium dioxide
37.2%-wt. of silicon dioxide
11.5%-wt. of polyethylene glycol 400
4.6%-wt. of polyethylene glycol 4000
10.2%-wt. of sorbitol.

B. Coating

Application device: rollers, coating box, nozzles.
Continuous coating on:
I. structured support (e.g. Teflon, special steel)
II. adhesively treated material (e.g. paper, film or foil) with planar surface
III: as under II.

C. Drying re I. By means of hot air.
re II. By means of hot air, with "warmer" and "colder" zones having to be provided.
   In this way, a foil-like band is obtained which has different thicknesses. At the warmer zones, the material is thicker, and at the colder zones it is thinner.
   These zones are obtained by
      a) an open-worked surface, e.g. lattice hole structure of the band-shaped support,
      b) use of materials with different heat conduction in the production of the conveyor belt,
      c) adhesively treated material in which segments with differing heat conduction properties are implanted.
re III. By means of hot air as under I., and additional use of a structured embossing roller.

D. Applying the Second Layer

The second layer is anchored on the first, structured layer by means of coating with a suitable mass which inter alia during the coating process does not entirely or partially dissolve or melt the first, structured layer.

E. Fabrication

1. Cutting lengthwise in narrow rolls.
2. Separating by punching or transverse cutting (in the case of II., the paper or the film or foil is first removed).
3. Packing.

Figure 2:
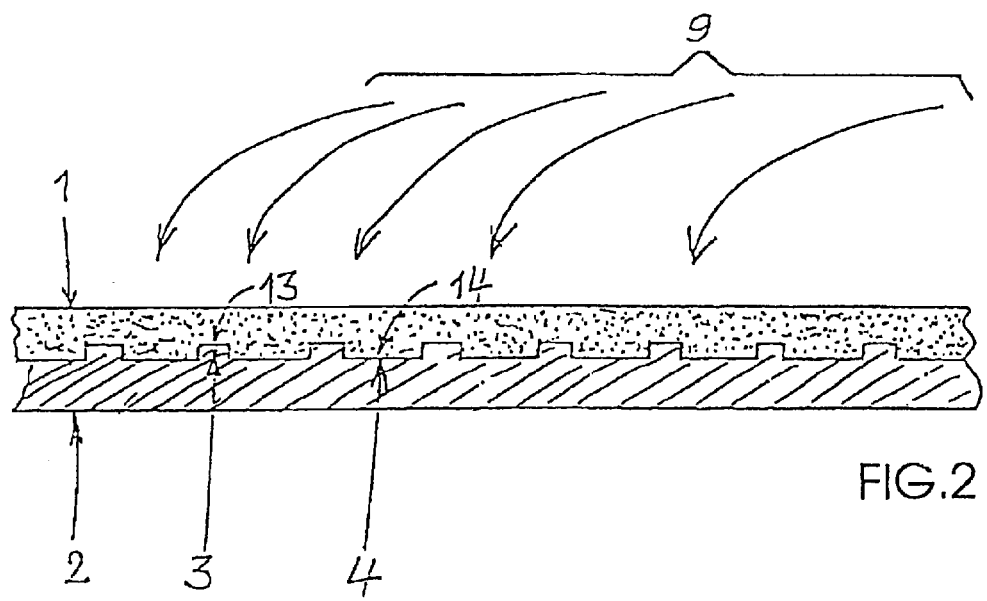
FIG. 2 shows production of the coding in the first layer on a support provided with differing thicknesses.
Figure 3:
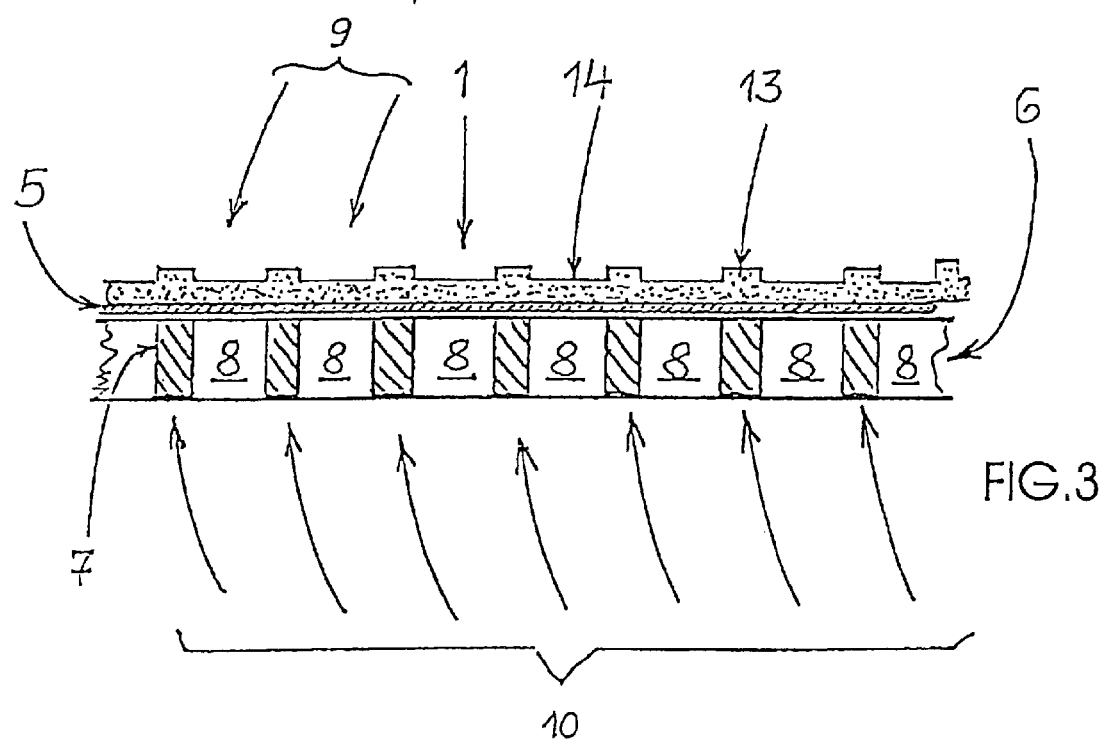
FIG. 3 shows the production of coding in the first layer using local temperature differences.

Further details, features and advantages of the invention will be evident from the following explanation of the illustrative embodiments which are shown diagrammatically in the drawings, in which:

FIG. 1 is a diagrammatic representation of the finished two-layered medicinal administration form (in cross section) provided with a coding, FIG. 2 is a diagrammatic representation (in cross section), with production of the coding in the first layer on a support provided with thickness differences, FIG. 3 shows (in cross section) the production of a coding in the first layer by means of subjecting the preparation to local temperature differences.

FIG. 1 shows the two-layer preparation with the structured first layer (1) and the reciprocal (=complementary) second layer (2), with the overall thickness being the same at every point.

FIG. 2 shows the first layer (1) of the preparation on a structured support (2) which has a sequence of elevations (3) and depressions (4). Correspondingly, depressions (13) develop reciprocally to the elevations (3), and elevations (14) develop reciprocally to the depressions (4) in the first layer (1) of the preparation. Heat is delivered in a heat stream (9), which can involve both radiation and also convection.

FIG. 3 shows a manufacturing method in which the thickness differences (13, 14) in the layer (1) of the preparation are produced using local temperature differences during drying. Here, the first layer (1) of the preparation lies on a foil-like carrier (5), for example silicone paper, aluminium foil, plastic film or the like. A conveyor belt is designated by (6), which has a lattice or hole structure consisting of bridges (7) and openings (8). By means of heat delivered to the bridges in accordance with the arrows (10), these form warmer areas in contact with the carrier film (5) and colder areas in the region of the openings (8). In the area of the warmer zones, the material turns out thicker on drying, while it is thinner in the colder areas.

Here, the drying can also be assisted from above, for example, by a stream (9) of heated air. The temperature differences of the conveyor belt (6) can be generated, for example, by inductive heating of the bridges (7) of the lattice structure or by radiation or contact heating, while the openings (8) are cooled, for example, by convection with air.

The invention is uncomplicated and optimally satisfies the object set out in the introduction.

What is claimed is:

1. A preparation for administering active substances comprising:
   a first layer;
   a second layer adjacent to the first layer, the second layer having a different color than the first layer; and
   coding in the form of at least one of characters, graphic symbols or patterns for identifying the active substances, the coding being formed by surface areas having differing thicknesses in each of the first and second layers, and the surface areas of differing thicknesses of the first layer are complementary to the surface areas of differing thickness of the second layer;
   wherein the preparation is a sheet, a film or a wafer.

2. The preparation according to claim 1, wherein the layers are opaque.

3. The preparation according to claim 1, wherein it comprises one or two additional layers which are transparent.

4. The preparation according to claim 1, wherein the surface areas of differing thickness do not exhibit differences in density or compression.

5. The preparation according to claim 1, wherein the surface areas of differing thickness have a different density.

6. A method for producing a preparation according to claim 1, which comprises forming the surface areas of differing thickness of the first layer without the action of pressure.

7. The method according to claim 6, wherein the thickness differences of the first layer are produced by coating of a support which has a sequence of elevations or depression corresponding to the coding.

8. The method according to claim 6, wherein the thickness differences of the first layer are produced by pre-determined local temperature differences during drying of the preparation.

9. A method for producing a preparation according to claim 1, which comprises forming the surface areas of differing thickness of the first layer under the action of pressure.

10. A method for producing a preparation according to claim 1, which comprises coding of the surface areas in the form of at least one of symbols, characters or patterns, the coding being produced by plastic deformation of the first layer.

11. The method according to claim 6, wherein the thickness differences are introduced into the layer in a discontinuous manner.

12. The method according to claim 6, wherein the thickness differences are introduced into the layer in a continuous manner.

13. A method for producing a preparation according to claim 1, comprising:
   providing the first layer with surface areas of differing thickness without the action of pressure;
   coating the first layer with a suitable mass to form the complementary second layer, the coating being performed by a knife application process, a roller application process, a spraying process or an extrusion process; and
   subsequent hardening of the mass.

14. A method for producing a preparation according to claim 1, comprising:
   providing the first layer with surface areas of differing thickness under the action of pressure;
   coating the first layer with a suitable mass to form the complementary second layer, the coating being performed by a knife application process, a roller application process, a spraying process or an extrusion process; and
   subsequent hardening of the mass.

15. A method for producing a preparation according to claim 1, comprising:
   providing the first layer with coding of the surface areas in the form of at least one of symbols, characters or patterns, the coding being produced by plastic deformation of the first layer;
   coating the first layer with a suitable mass to form the complementary second layer, the coating being performed by a knife application process, a roller application process, a spraying process or an extrusion process; and
   subsequent hardening of the mass.

16. The preparation according to claim 1, wherein the active substance is at least one of a flavorant, a colorant, a therapeutic substance or a curative substance.

* * * * *